United States Patent
Parant et al.

(10) Patent No.: US 9,179,668 B2
(45) Date of Patent: Nov. 10, 2015

(54) USE OF GLYCEROL ETHERS AS ACTIVATORS OF THE BIOLOGICAL EFFECTS OF A HERBICIDE, FUNGICIDE OR INSECTICIDE SUBSTANCE

(75) Inventors: Bernard Parant, Ozoir la Ferriere (FR); Emmanuel Roussel, Fontenay Tresigny (FR); Yann Raoul, Crezancy (FR)

(73) Assignee: FONDS DE DEVELOPPEMENT DES FILIERES DES OLEAGINEUX ET PROTEAGINEUX FIDOP, Paris (FR)

( * ) Notice: Subject to any disclaimer, the term of this patent is extended or adjusted under 35 U.S.C. 154(b) by 825 days.

(21) Appl. No.: 13/394,510

(22) PCT Filed: Sep. 8, 2010

(86) PCT No.: PCT/FR2010/051875
§ 371 (c)(1),
(2), (4) Date: May 7, 2012

(87) PCT Pub. No.: WO2011/030061
PCT Pub. Date: Mar. 17, 2011

(65) Prior Publication Data
US 2012/0214671 A1    Aug. 23, 2012

(30) Foreign Application Priority Data
Sep. 8, 2009   (FR) ...................................... 09 56102

(51) Int. Cl.
*A01N 57/18*    (2006.01)
*A01N 31/02*    (2006.01)
(52) U.S. Cl.
CPC ...................................... *A01N 31/02* (2013.01)

(58) Field of Classification Search
None
See application file for complete search history.

(56) References Cited

U.S. PATENT DOCUMENTS 6,482,773 B1 *   11/2002   Katayama et al. ............ 504/225
2005/0031653 A1 *   2/2005   Kwetkat et al. ............... 424/401

FOREIGN PATENT DOCUMENTS

| EP | 0 503228 | 9/1992 |
| EP | 0 968 649 | 1/2000 |
| EP | 1 344 454 | 3/2009 |
| EP | 2 036 437 | 3/2009 |
| WO | WO03/090531 | 11/2003 |

* cited by examiner

*Primary Examiner* — Alton Pryor
(74) *Attorney, Agent, or Firm* — Hamre, Schumann, Mueller & Larson, P.C.

(57) ABSTRACT

The invention relates to the use of glycerol ethers as agents that activate the biological effects of at least one substance selected from a herbicide, fungicide or insecticide. The invention essentially relates to the use of glycerol ether as an agent that activates the biological effects of at least one substance selected from a herbicide, or fungicide or insecticide, said glycerol ether having formula (1), wherein $R_1$ represents an alkyl group having between 1 and 18 carbon atoms and $R_2$ represents a hydrogen atom or an alkyl group having between 1 and 18 carbon atoms, preferably a methyl or ethyl group. The invention also relates to a phytosanitary composition containing one such glycerol ether, as well as to a phytosanitary treatment method using said composition.

11 Claims, No Drawings

USE OF GLYCEROL ETHERS AS ACTIVATORS OF THE BIOLOGICAL EFFECTS OF A HERBICIDE, FUNGICIDE OR INSECTICIDE SUBSTANCE

The present invention relates generally to novel compositions comprising at least one active substance chosen from a herbicide, an insecticide or a fungicide and has as subject matter essentially the use of certain glycerol ethers as activators which make it possible to intensify the biological effects of at least one active substance chosen from a herbicide, an insecticide or a fungicide.

The invention finds application in particular in the agricultural field.

The glycerol ethers used in the context of the present invention are mono- or dialkylated derivatives of glycerol. These compounds are generally known in the state of the art.

Thus, 3-(2-ethylhexyloxy)propane-1,2-diol (also known as ethylhexylglycerin), which is one of the compounds preferably used in the context of the present invention, is known in the cosmetics field, where it is used in particular as scent enhancer in deodorant formulations.

It has been discovered, and this constitutes the basis of the present invention, that some glycerol ethers exhibit the noteworthy property of accelerating the passage of various active substances through the cell membranes of unicellular or multicellular inhabitants of the animal or plant kingdom and that this noteworthy property makes it possible:

(1) in the context of their use in combination with a herbicidal substance:
on the one hand, to increase the rate of weed elimination in so far as the lethal threshold for the plant is reached more rapidly; and
on the other hand, to decrease by a factor of 2 to 4 the minimum amount of herbicidal substance to be employed in order to obtain the desired effect;

(2) in the context of their use in combination with a fungicidal substance, to decrease the minimum amount of fungicidal substance to be employed in order to obtain the desired effect;

(3) in the context of their use in combination with an insecticidal substance, to significantly increase the mortality rate in the insects treated.

Thus, according to a first aspect, the subject matter of the invention is the use of a glycerol ether of formula:

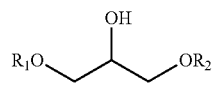

(I)

in which:
$R_1$ represents an alkyl group having from 1 to 18 carbon atoms;
$R_2$ represents a hydrogen atom or an alkyl group having from 1 to 18 carbon atoms, preferably a methyl or ethyl group; as agent to enhance the biological effects of at least one active substance chosen from a herbicide, a fungicide or an insecticide.

The enhancing effect of the glycerol ethers with respect to a herbicidal substance is understood to mean
on the one hand, the effect of increasing the rate of weed elimination for a given concentration of active substance; and
on the other hand, an effect of potentiating the activity of the herbicidal substance, making it possible to decrease the amount to be employed in order to obtain the desired effect.

A first preferred family of glycerol ethers capable of being used in the context of the present invention is composed of the compounds of abovementioned formula (I) in which:
$R_1$ represents an alkyl group of general formula $C_xH_{2x+1}$ where x=1 to 9;
$R_2$ represents an alkyl group of general formula $C_yH_{2y+1}$ where y=0 to 8; and observing the condition $4 \leq x+y \leq 10$.

Another preferred family of glycerol ethers capable of being used in the context of the present invention is composed of the monoalkylated glycerol compounds of abovementioned formula (I), in which:
$R_3$ represents an alkyl group having from 4 to 9 carbon atoms; and
$R_2$ represents a hydrogen atom.

Particularly noteworthy results have been obtained with 3-pentyloxypropane-1,2-diol, 3-hexyloxypropane-1,2-diol and 3-(2-ethylhexyloxy)propane-1,2-diol, which consequently constitute particularly preferred compounds for the use thereof as enhancer (activator) of the biological effect of a herbicidal, fungicidal or insecticidal substance in the context of the present invention.

Another preferred family of glycerol ethers capable of being used in the context of the present invention is composed of the dialkylated glycerol compounds of abovementioned formula (I), in which:
$R_1$ represents a methyl or ethyl group; and
$R_2$ represents a methyl or ethyl group.

Preferably, $R_1$ and $R_2$ are identical in these dialkylated compounds of formula (I).

The abovementioned glycerol ethers of formula (I) act as activators of the herbicidal effects of any herbicidal substance.

"Alkyl group" is understood to mean a linear or branched hydrocarbon group.

Any known herbicidal, fungicidal and insecticidal substance can be used in the context of the present invention.

Mention may be made, among the herbicidal substances which can be used in the context of the invention, of:
lipid synthesis inhibitors, such as, in particular:
aryloxyphenoxypropionates (clodinafop-propargyl, diciofop-methyl, fenoxaprop-P-ethyl, fluazifop-P-butyl, quizalofop-P-ethyl, haloxyfop-R, propaquizafop),
cyclohexanediones (clethodim, cycloxydim, sethoxydim, t koxydim),
benzofurans (ethofumesate);
acetolactase synthase (ALS) inhibitors, such as, in particular:
imidazolinones (imazamox, imazapyr, imazethapyr, imazaquin),
sulfonylureas (amidosulfuron, azimsulfuron, bensulfuron-methyl, chlorimuron, chlorsulfuron, ethametsulfuron-methyl, flazasulfuron, flupyrsulfuron-methyl-sodium, foramsulfuron, iodosulfuron-methyl-sodium, mesosulfuron-methyl, metsuffuron-methyl, nicosulfuron, primisulfuron, prosulfuron, rimsulfuron, sulfosulfuron, thifensulfuron-methyl, tribenuron-methyl, triflusulfuron-methyl),
sulfonanilides (cloransularn, flumetsulam, florasulam),
triazolopyrim idines (pyroxsulam);
inhibitors of the synthesis of aromatic amino acids, such as, in particular:

glyphosate in the isopropylamine salt form or in the trimethylsulfonium salt form (sulfosate);

auxin herbicides, such as, in particular:
- phenoxy adds (2,4-D, 2,4-DB, 2,4,5-T, dichlorprop, MCPA, MCPB, mecoprop),
- benzoic adds (dicamba),
- pyridinic acids (clopyralid, picloram, triclopyr),
- quinmerac;

pigment inhibitors, such as, in particular:
- triazoles (amitrole, clomazone),
- isoxazolidinones (clomazone),
- isoxazoles (isoxaflutole),
- triketones (mesotrione, sulcotrione),
- diphenyl ethers (aclonifen),
- phenoxybutamide (beflubutamid),
- fluorochloridone,
- flurtamone;

photosynthesis inhibitors, such as, in particular:
- triazines (atrazine, cyanazine, hexazinone, metribuzin, prometryn, simazine),
- uracils (lenacil, bromacil, terbacil),
- phenylcarbamates (desmedipharn, phenmedipham),
- pyridazinones (pyrazon),
- substituted ureas (isoproturon, diuron, linuron, chlortoluron, metobromuron, monolinuron),
- phenylpyridazines (pyridate),
- benzothiadiazones (bentazone),
- nitriles (bromoxynil, ioxynil);

plantlet growth inhibitors, such as, in particular:
- dinitroanilines (ethalfluralin, pendimethalin,
- benzamides (propyzamide),
- pyridines (dithiopyr),
- carbamates (carbetamide),
- carbamothioates (butylate, cycloate, EPTC, trialiate),
- phosphorodithioates (bensulide),
- chloroacetamides (alachlor, acetoch or, dimethenamid, dimethachlor, flufenacet, metazachlor, S-metolachlor),
- acetamides (napropamide);

herbicides which disrupt the cell membranes, such as, in particular:
- phosphorylated amino acids (glufosinate, glufosinate-ammonium),
- diphenyl ethers (acifluorfen, fomesafen, oxyfluorfen, bifenox),
- oxadiazoles (oxidiazon, oxadiargyl),
- dipyridyls (difenzoquat, paraquat, diquat),
- benzamides (isoxaben),
- nitriles (dichlobenil);

triazinone (metamitron);

herbicidal substances not listed in the preceding categories (bispyribac-sodium, diflufenican, lactofen, norflurazon)

Mention may be made, as herbicidal substances preferred in the context of the present invention, of the following substances:
- dichlobenil (ornamental trees and bushes);
- ethofumesate (fodder beet, sugar beet);
- glyphosate-isopropylammonium (general treatments);
- glufosinate-ammonium (general treatments);
- isoproturon (soft winter wheat, winter barley);
- linuron (vegetable crops, sunflower);
- metamitron (fodder beet, sugar beet, garden beet);
- oxyfluorfen/propyzamide (vines, orchards, ornamental trees and bushes);
- phenmedipham (fodder beet, sugar beet, garden beet);
- trifluralin (rape, winter rape, spring rape, sunflower, soya).

Particularly noteworthy results were obtained with glyphosate in the isopropylamine salt form, which constitutes one of the most widely used herbicidal substances in the world.

Mention may be made, among the fungicidal substances which can be used in the context of the invention, of:
- polyvalent or multisite substances: dithiocarbamates (mancozeb, maneb, zineb, ziram, thiram), chloronitriles (chlorothalonil), phthalimides (captan, folpel), sulfamides (tolylfluanid) and guanidines (dodine);
- substances which inhibit mitochondrial respiration: phenylamides (carboxin, flutolanil), methyl β-methoxyacrylates (azoxystrobin, picoxystrobin), cyanoimidazoles (cyazofamid), imidazolinones (fenamidone), oxazolidinediones (famoxadone), methyl methoxyacetates (kresoxim-methyl), methyl methoxycarbamates (pyraclostrobin), nitrophenyl crotonates (dinocap), dinitroanilines (fluazinam), silylamide (silthiofam);
- substances which inhibit the biosynthesis of lipids, such as, in particular: dicarboximides (iprodione, procymidone, vinclozolin), organophosphorus compounds (tolclofos-methyl), carbamates (propamocarb);
- substances which inhibit the biosynthesis of membrane sterols: pyrimidines (fenarimol, nuarimol), imidazoles (imazalil, prochloraz), triazoles (bitertanol, difenoconazole, flusilazole, propiconazole, triadimenol), hydroxyanilides (fenhexamid), morpholines (dodemorph, fenpropimorph, tridemorph), piperidines (fenpropidin), spiroketalamine (spiroxamine);
- substances which inhibit the synthesis of nucleic acids: phenylamides (benalaxyl, mefenoxam), hydroxypyrimidines (bupirimate), hyrnexazol;
- substances which act on the formation of cell walls: acetamides (cymoxanil), dimethomorph, amino acid carbamate (iprovalicarb);
- substances which affect signal transduction: quinolines (quinoxyfen), phenylpyrroles (fludioxonil);
- substances which inhibit the biosynthesis of methionine: anilinopyrimidines (cyprodinil, pyrimethanil, mepanipyrim);
- substances which affect the assembling of β-tubulin: benzamides (zoxamide), phenylureas (pencycuron), benzimidazoles (carbendazim, thiabendazole), N-phenylcarbamates (diethofencarb);
- natural substances, such as essential oils (clove, bay, savory, thyme, *Melaleuca alternifolia*, geranium);
- and the fungicidal substances not listed in the preceding categories.

Mention may be made, as fungicidal substances which are preferred in the context of the present invention, of the following substances:
- azoxystrobin, pyraclostrobin, difenoconazole, fenpropimorph, mancozeb, cyproconazole, metconazole, tebuconazole, prothioconazole, prochloraz, boscalid (indicated for the cultivation of oleaginous plants).

Mention may be made, among insecticidal substances which can be used in the context of the invention, of:
- substances which act on the nervous system: organophosphorus compounds (dichlorvos, dimethoate, chlorpyrifos, parathion, malathion, diazinon, phosmet), carbamates (carbofuran, carbaryl, methomyl, aldicarb, carbosulfan, fenoxycarb), pyrethroids (permethrin, deltamethrin, cypermethrin, fenvalerate, tefluthrin), phenylpyrazoles (fipronil), avermectins (ivermectin, selamectin, milbemectin, and the like), chloronicotinoids (imidacloprid, nitenpyram, thiamethoxam), formamidines (amitraz);

substances which act on cellular respiration: amidinohydrazones (hydramethylnon), rotenones (rotenone), pyrazoles (fenpyroximate, tebufenpyrad), stannic derivatives (azocyclotin, cyhexatin), sulfones/sulfonates (chlorfenson, tetradifon);

substances which act on the growth of the insect: benzoylureas and acylureas (diflubenzuron, hexaflumuron, lufenuron, teflubenzuran, flufenoxuron), benzhydrazides (tebufenozide, methoxyfenozide);

natural substances, such as essential oils (thyme, aniseed, garlic, lavender, lemon, eucalyptus, mint, and the like) and pyrethrum (pyrethrins);

insecticidal substances not listed in the preceding categories: spinosyns (spinetoram), methoprene, pyriproxyfen.

Mention may be made, as insecticidal substances which are preferred in the context of the present invention, of the following substances:

tau-fluvalinate, lambda-cyhalothrin, pirimicarb, alphamethrin, beta-cyfluthrin, bifenthrin, cyfluthrin, cypermethrin, deltamethrin, esfenvalerate, zeta cypermethrin, thiacloprid, chlorpyrifos-ethyl, diflubenzuron (indicated for the cultivation of oleaginous plants).

Of course, the glycerol ethers according to the invention can be used to enhance the biological effects of a herbicidal, fungicidal or insecticidal substance used alone or as a mixture with at least one other herbicidal, fungicidal or insecticidal substance.

At least two glycerol ethers according to the invention can also be used in combination to enhance the biological effects of a herbicidal, fungicidal or insecticidal substance. Thus, for example, a mixture of at least one monoalkylated glycerol ether according to the invention and of at least one dialkylated glycerol ether according to the invention can be used to enhance the biological effects of a herbicidal, fungicidal or insecticidal substance.

Generally, the glycerol ethers will be used in an amount by weight of between 0.05 and 2, expressed relative to the amount by weight of herbicidal substance(s) used, an amount by weight of between 0.01 and 10, expressed relative to the amount by weight of fungicidal substance(s) used, or an amount by weight of between 0.05 and 2, expressed relative to the amount by weight of insecticidal substance(s) used.

According to a second aspect, a subject matter of the present invention is a plant-protection composition comprising:

at least one active substance chosen from a herbicide, an insecticide or a fungicide; and at least one glycerol ether of formula (I) as defined above, Plant-protection composition is understood to mean a composition capable of treating or preventing diseases of plant organisms and preferably having herbicidal and/or fungicidal and/or insecticidal effects.

Advantageously, this composition will comprise:

one (or more) herbicidal substance(s) in an overall amount of 100 parts by weight; and one (or more) glycerol ether(s) of formula (I) in an overall amount of 5 to 200 parts by weight, expressed relative to the amount by weight of herbicidal substance(s) used; or one (or more) fungicidal substance(s) in an overall amount of 100 parts by weight; and one (or more) glycerol ether(s) of formula (I) in an overall amount of 10 to 1000 parts by weight, expressed relative to the amount by weight of fungicidal substance(s) used; or one (or more) insecticidal substance(s) in an overall amount of 100 parts by weight; and one (or more) glycerol ether(s) of formula (I) in an overall amount of 5 to 200 parts by weight, expressed relative to the amount by weight of insecticidal substance(s) used.

Given that the abovementioned glycerol ethers are liquids and are soluble in the main organic solvents, a herbicidal composition according to the invention will advantageously be provided in the form of a liquid solution preferably comprising from 0.5 to 3 g/l and more preferably from 0.8 to 1 g/l of glycerol ether of formula (I).

Likewise, a fungicidal composition according to the invention will advantageously be provided in the form of a solution comprising from 0.01 to 3 g/l and preferably from 0.05 to 0.25 g/l of glycerol ether of formula (I).

An insecticidal composition according to the invention will, for its part, be provided in the form of a solution comprising from 0.01 to 3 g/l and preferably from 0.01 to 0.25 g/l of glycerol ether of formula (I).

Such a composition can comprise anionic, nonionic, cationic or amphoteric surfactants, so as to improve the wetting power of the composition. The only rule to be observed will be to use the surfactant at a concentration at least equal to the CMC (critical micelle concentration) during the spraying. It will also be possible to introduce colorants into this composition, so as to facilitate the identification of the composition by the user.

Mention may be made, as example of cationic surfactant capable of being used, of polyoxyethylene amine (POEA).

Mention may be made, as an example of anionic surfactant capable of being used, of alkali metal, in particular sodium, alkyl sulfates, such as in particular products sold under the name Melioran 118® by LECA.

Preferably, the plant-protection composition according to the invention comprises a content by weight of a surface-active agent as mentioned above, with respect to the total weight of the composition, chosen from at most approximately 66%, at most 50%, at most 40%, at most 30%, at most 20%, at most 10% or at most 5%, and more preferably does not comprise any surface-active agent.

The glycerol monoethers (or monoalkylated glycerol ethers) used in the context of the present invention (compounds of formula (I) in which $R_2$ represents a hydrogen atom) are generally commercial products. Alternatively, these products can be prepared by the reaction, preferably in a basic medium, of glycidol and an appropriate alcohol used in a large excess.

Generally, the molar ratio of the alcohol to the glycidol can vary between 5 and 20, while the molar ratio of the base (catalyst) to the glycidol can vary between 0.04 and 0.2.

This reaction can be represented by the following reaction scheme:

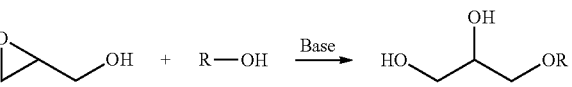

Generally, this reaction is carried out at a temperature of between 40 and 150° C.

In a first step, the alkoxide is formed under vacuum, at the synthesis temperature.

The glycidol (pure or diluted in the alcohol) is subsequently added to the reaction medium. To avoid any decomposition due to the presence of water, it is preferable to operate in an anhydrous medium, a low vacuum being applied.

The reaction time is of the order of 30 complete consumption of the glycidol.

The resulting product is distilled and, in a first step, the residual alcohol is obtained and then the desired glycerol ether is obtained.

The "symmetrical" glycerol diethers used in the context of the present invention (compounds of formula (I) in which $R_1$ and $R_2$ are identical and different from a hydrogen atom) may be commercial products. Alternatively, these products may be prepared by the reaction, preferably in a basic medium, of epichlorohydrin and an appropriate alcohol used in large excess.

Generally, the molar ratio of the alcohol to the epichlorohydrin can vary between 2 and 6, while the molar ratio of the base (catalyst) to the epichlorohydrin can vary between 0.3 and 2.0.

This reaction can be represented by the following reaction scheme:

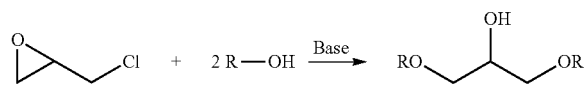

Generally, this reaction is carried out at a temperature of between 40 and 150° C.

In a first step, the alkoxide is formed under vacuum, at the synthesis temperature.

Epichlorohydrin (pure or diluted in the alcohol) is subsequently added to the reaction medium. To avoid any decomposition due to the presence of water, it is preferable to operate in an anhydrous medium, a low vacuum being maintained.

The reaction time is of the order of 3 hours for complete consumption of the epichlorohydrin.

The resulting product is distilled and, in a first step, the residual alcohol is obtained and then the desired glycerol diether is obtained.

The "asymmetrical" glycerol diethers used in the context of the present invention (compounds of formula (I) in which $R_1$ and $R_2$ are different from one another and each is different from a hydrogen atom) may be commercial products. Alternatively, these products may be prepared by the reaction, preferably in a basic medium, of the glycerol monoether of formula:

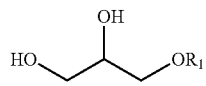

and an appropriate alcohol used in large excess.

Generally, the molar ratio of the alcohol to the glycerol monoether can vary between 2 and 6, while the molar ratio of the base (catalyst) to the glycerol monoether can vary between 0.3 and 2.0.

This reaction can be represented by the following reaction scheme:

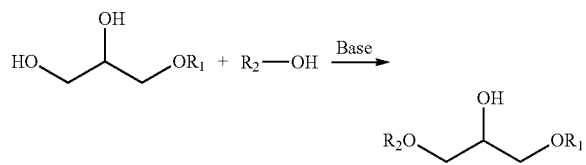

Generally, this reaction is carried out at a temperature of between 40 and 150° C.

In a first step, the alkoxide is formed at the synthesis temperature.

The glycerol monoether is subsequently added to the reaction medium. To avoid any decomposition due to the presence of water, it is preferable to operate in an anhydrous medium, a low vacuum being maintained.

The reaction time is of the order of 5 hours for complete consumption of the glycerol monoether.

The resulting product is distilled and, in a first step, the residual alcohol is obtained and then the desired glycerol diether is obtained.

According to a third aspect, a subject matter of the present invention is a plant-protection treatment method chosen from a herbicidal treatment, a fungicidal treatment and an insecticidal treatment, which consists in applying a plant-protection composition as defined above to a surface to be treated.

Generally, in the context of a herbicidal treatment method, the glycerol ethers will be applied in an amount of between 100 and 1500 g, preferably between 150 and 1350 g, of active material per hectare of surface area to be weeded.

In the context of a fungicidal treatment method, the amount of glycerol ethers applied will be between 50 and 5000 g, preferably between 150 and 4500 g, per hectare of surface area to be treated.

In the context of an insecticidal treatment method, the amount of glycerol ethers applied will be between 40 and 1000 g, preferably between 75 and 750 g, per hectare of surface area to be treated.

The invention will now be illustrated by the following nonlimiting examples.

A—Examples of the Preparation of a Glycerol Ether Used in the Context of the Present Invention Preparation 1

Isononyl alcohol (Exxal® 9, sold by Exxon Mobil Corporation) and sodium hydroxide were introduced, in a molar ratio of 10:0.1, into a container of 250 ml to 20 l which is provided with stirring ranging from 150 to 300 rpm, is heated to 120° C. and is at atmospheric pressure.

The reaction between the alcohol and the sodium hydroxide was carried out under vacuum at 120° C. in order to result in the formation of the alkoxide.

Glycidol was subsequently introduced in an amount such that the molar ratio of the isononyl alcohol to the glycidyl is 10:1 (this introduction is carried out at atmospheric pressure over a period of time of 15 min).

Consumption of the glycidyl was complete from the end of the introduction.

The reaction mixture was purified by distillation.

Thus, the isononyl alcohol was first obtained (113-115° C. under 20-25 mb), followed by the glycerol ether (191-215° C. under 20-25 mb), Yield: 27.6%.

Preparation 2

The preparation was carried out analogously to preparation 1.

The alcohol/glycidol/sodium hydroxide molar ratio was 6:1:0.1.

The alkoxide was formed under vacuum at 80° C. with half the total amount of the alcohol and the sodium hydroxide.

The glycidyl, diluted beforehand in the second half of the alcohol, was introduced under 20-25 mb over a period of time of 15 min.

The consumption of glycidol was complete from the end of the introduction.

The reaction mixture was purified by distillation. Thus, the alcohol was first obtained (113-115° C. under 20-25 mb), followed by the glycerol ether (191-215° C. under 20-25 mb).

Yield: 30%.

B—Demonstration of the Properties of Enhancing Herbicidal Effects of Glycerol Ethers The following tests were carried out on plots of land of 50×50 cm on which herbaceous plants occur. Each of the solutions tested is sprayed over a plot which is assigned to it.

EXAMPLE 1

The time necessary for the complete destruction of the vegetation was compared, on similar plots planted with herbaceous plants, with a herbicide alone, on the one hand, and the same herbicide to which has been added a glycerol ether: 3-methyloxypropane-1,2-diol, on the other hand.

A solution comprising 6 g/l of glyphosate (in the acid form) was sprayed over plot 1 in a proportion of 36 grams to the $m^2$.

A solution comprising 6 of glyphosate and 0.9 g/l of 3-methyl-oxypropane-1,2-diol was sprayed over plot 2 in a proportion of 36 grams to the $m^2$.

On plot 1, it was observed:
 that deterioration began after 8 days
 that deterioration was complete after 18 days.
On plot 2, it was observed;
 that deterioration began after 4 days
 that deterioration was complete after 13 days.

EXAMPLE 2

The time necessary for the complete destruction of the vegetation was compared, on similar plots planted with herbaceous plants, with a herbicide alone, on the one hand, and the same herbicide to which has been added a glycerol ether: 1,3-dimethyloxypropan-2-ol, on the other hand.

A solution comprising 6 g/l of glyphosate was sprayed over plot 1 in a proportion of 36 grams to the $m^2$.

A solution comprising 6 g/l of glyphosate and 0.9 g/l of 1,3-dimethyl-oxypropan-2-ol was sprayed over plot 2 in a proportion of 36 grams to the $m^2$.

On plot 1, it was observed:
 that deterioration began after 8 days
 that deterioration was complete after 18 days.
On plot 2, it was observed:
 that deterioration began after 4 days
 that deterioration was complete after 15 days.

EXAMPLE 3

The time necessary for the complete destruction of the vegetation was compared, on similar plots planted with herbaceous plants, with a herbicide alone, on the one hand, and the same herbicide to which has been added a glycerol ether: 3-isopropyloxypropane-1,2-diol, on the other hand.

A solution comprising 6 g/l of glyphosate was sprayed over plot 1 in a proportion of 36 grams to the $m^2$.

A solution comprising 6 g/l of glyphosate and 0.9 g/l of 3-isopropyl-oxypropane-1,2-diol was sprayed over plot 2 in a proportion of 36 grams to the $m^2$.

On plot 1, it was observed:
 that deterioration began after 8 days
 that deterioration was complete after 18 days,
On plot 2, it was observed:
 that deterioration began after 3 days
 that deterioration was complete after 12 days.

EXAMPLE 4

The time necessary for the complete destruction of the vegetation was compared, on similar plots planted with herbaceous plants, with a herbicide alone, on the one hand, and the same herbicide to which has been added a glycerol ether: 3-butyloxypropane-1,2-diol, on the other hand.

A solution comprising 6 g/l of glyphosate was sprayed over plot 1 in a proportion of 36 grams to the $m^2$.

A solution comprising 6 g/l of glyphosate and 0.9 g/l of 3-butyl-oxypropane-1,2-diol was sprayed over plot 2 in a proportion of 36 grams to the $m^2$.

On plot 1, it was observed:
 that deterioration began after 8 days
 that deterioration was complete after 18 days,
On plot 2, it was observed:
 that deterioration began after 3 days
 that deterioration was complete after 10 days.

EXAMPLE 5

The time necessary for the complete destruction of the vegetation was compared, on similar plots planted with herbaceous plants, with a herbicide alone, on the one hand, and the same herbicide to which has been added a glycerol ether: 3-ethyloxypropane-1,2-diol, on the other hand.

A solution comprising 6 g/l of glyphosate was sprayed over plot 1 in a proportion of 36 grams to the $m^2$.

A solution comprising 6 of glyphosate and 0.9 g/l of 3-ethyl-oxypropane-1,2-diol was sprayed over plot 2 in a proportion of 36 grams to the $m^2$.

On plot 1, it was observed:
 that deterioration began after 8 days
 that deterioration was complete after 18 days.
On plot 2, it was observed:
 that deterioration began after 3 days
 that deterioration was complete after 11 days.

EXAMPLE 6

The time necessary for the complete destruction of the vegetation was compared, on similar plots planted with herbaceous plants, with a herbicide alone, on the one hand, and the same herbicide to which has been added a glycerol ether: 1,3-diethyloxypropan-2-ol, on the other hand.

A solution comprising 6 g/l of glyphosate was sprayed over plot 1 in a proportion of 36 grams to the $m^2$.

A solution comprising 6 g/l of glyphosate and 0.9 g/l of 1,3-diethyl-oxypropan-2-ol was sprayed over plot 2 in a proportion of 36 grams to the $m^2$.

On plot 1, it was observed:
 that deterioration began after 8 days
 that deterioration was complete after 18 days.
On plot 2, it was observed:
 that deterioration began after 4 days
 that deterioration was complete after 13 days.

EXAMPLE 7

The time necessary for the complete destruction of the vegetation was compared, on similar plots planted with herbaceous plants, with a herbicide alone, on the one hand, and the same herbicide to which has been added a glycerol ether: 3-pentyloxypropane-1,2-diol, on the other hand.

A solution comprising 6 g/l of glyphosate was sprayed over plot 1 in a proportion of 36 grams to the $m^2$.

A solution comprising 6 g/l of glyphosate and 0.9 g/l of 3-pentyl-oxypropane-1,2-diol was sprayed over plot 2 in a proportion of 36 grams to the $m^2$.

On plot 1, it was observed:
 that deterioration began after 8 days
 that deterioration was complete after 18 days.

On plot 2, it was observed:
    that deterioration began after 3 days
    that deterioration was complete after 10 days.

EXAMPLE 8

The time necessary for the complete destruction of the vegetation was compared, on similar plots planted with herbaceous plants, with a herbicide alone, on the one hand, and the same herbicide to which has been added a glycerol ether: 3-hexyloxypropane-1,2-diol, on the other hand.

A solution comprising 6 g/l of glyphosate was sprayed aver plot 1 in a proportion of 36 grams to the $m^2$.

A solution comprising 6 g/l of glyphosate and 0.9 g/l of 3-hexyl-oxypropane-1,2-diol was sprayed over plot 2 in a proportion of 36 grams to the $m^2$.

On plot 1, it was observed:
    that deterioration began after 8 days
    that deterioration was complete after 18 days.
On plot 2, it was observed:
    that deterioration began after 3 days
    that deterioration was complete after 10 days.

EXAMPLE 9

The time necessary for the complete destruction of the vegetation was compared, on similar plots planted with herbaceous plants, with a herbicide alone, on the one hand, and the same herbicide to which has been added a glycerol ether: 3-(2-ethylhexyloxy)propane-1,2-diol, on the other hand.

A solution comprising 6 g/l of glyphosate was sprayed over plot 1 in a proportion of 36 grams to the $m^2$.

A solution comprising 6 g/l of glyphosate and 0.9 g/l of 3-(2-ethylhexyl oxy)propane-1,2-diol was sprayed over plot 2 in a proportion of 36 grams to the $m^2$.

On plot 1, it was observed:
    that deterioration began after 8 days
    that deterioration was complete after 18 days.
On plot 2, it was observed:
    that deterioration began after 3 days
    that deterioration was complete after 11 days.

EXAMPLE 10

The time necessary for the complete destruction of the vegetation was compared, on similar plots planted with herbaceous plants, with a herbicide alone, on the one hand, and the same herbicide to which has been added a glycerol ether: 3-decyloxypropane-1,2-diol, on the other hand.

A solution comprising 6 of glyphosate was sprayed over plot 1 in a proportion of 36 grams to the $m^2$.

A solution comprising 6 g/l of glyphosate and 0.9 g/l of 3-decyl-oxypropane-1,2-diol was sprayed over plot 2 in a proportion of 36 grams to the $m^2$.

On plot 1, it was observed:
    that deterioration began after 8 days
    that deterioration was complete after 18 days.
On plot 2, it was observed:
    that deterioration began after 4 days
    that deterioration was complete after 11 days.

EXAMPLE 11

The following sprayings were carried out on 4 plots covered with herbaceous plants:
    Plot 1: glyphosate at 6 g/l (36 g of the solution to the $m^2$)
    Plot 2: glyphosate at 4.5 g/l (36 g of the solution to the $m^2$)
    Plot 3: a solution of glyphosate at 1.5 g/l 3-pentyloxypropane-1,2-diol at 0.9 g/l, in a proportion of 36 g of the solution to the $m^2$.
    Plot 4: a solution of glyphosate at 0.75 WI 3-pentyloxypropane-1,2-diol at 0.9 g/l, in a proportion of 36 g of the solution to the $m^2$.

It was observed that, after 30 days, plots 1 and 3 have completely deteriorated, whereas plots 2 and 4 are unaffected.

EXAMPLE 12

The following sprayings were carried out on 4 plots covered with herbaceous plants:
    Plot 1: glyphosate at 6 g/l (36 g of the solution to the $m^2$)
    Plot 2: glyphosate at 4.5 g/l (36 g of the solution to the $m^2$)
    Plot 3: a solution of glyphosate at 3 g/l+3-butyloxypropane-1,2-diol at 0.9 g/l, in a proportion of 36 g of the solution to the $m^2$
    Plot 4: a solution of glyphosate at 1.5 g/l+3-butyloxypropane-1,2-diol at 0.9 g/l, in a proportion of 36 g of the solution to the $m^2$.

It was observed that, after 30 days, plots 1 and 3 have completely deteriorated, whereas plots 2 and 4 are unaffected.

EXAMPLE 13

The following sprayings were carried out on 4 plots covered with herbaceous plants:
    Plot 1: glyphosate at 6 g/l (36 g of the solution to the $m^2$)
    Plot 2: glyphosate at 4.5 g/l (36 g of the solution to the $m^2$)
    Plot 3: a solution of glyphosate at 3 g/l+3-hexyloxypropane-1,2-diol at 0.9 g/l, in a proportion of 36 g of the solution to the $m^2$
    Plot 4: a solution of glyphosate at 1.5 g/l+3-hexyloxypropane-1,2-diol at 0.9 g/l, in a proportion of 36 g of the solution to the $m^2$.

It was observed that, after 30 days, plots 1 and 3 have completely deteriorated, whereas plots 2 and 4 are unaffected.

EXAMPLE 14

The following sprayings were carried out on 4 plots covered with herbaceous plants:
    Plot 1: glyphosate at 6 g/l (36 g of the solution to the $m^2$)
    Plot 2: glyphosate at 4.5 g/l (36 g of the solution to the $m^2$)
    Plot 3: a solution of glyphosate at 3 g/l+3-(2-ethylhexyloxy)propane-1,2-diol at 0.9 g/l, in a proportion of 36 g of the solution to the $m^2$
    Plot 4: a solution of glyphosate at 1.5 g/l+3-(2-ethylhexyloxy)propane-1,2-diol at 0.9 g/l, in a proportion of 36 g of the solution to the $m^2$.

It is observed that, after 30 days, plots 1 and 3 have completely deteriorated, whereas plots 2 and 4 are unaffected.

EXAMPLE 15

The following sprayings were carried out on 4 plots covered with herbaceous plants:
    Plot 1: glyphosate at 6 g/l (36 g of the solution to the $m^2$)
    Plot 2: glyphosate at 4.5 g/l (36 g of the solution to the $m^2$)
    Plot 3: a solution of glyphosate at 3 g/l+3-isopropyloxypropane-1,2-diol at 0.9 g/l, in a proportion of 36 g of the solution to the $m^2$.
    Plot 4: a solution of glyphosate at 1.5 g/l+3-isopropyloxypropane-1,2-diol at 0.9 in a proportion of 36 g of the solution to the $m^2$.

It was observed that, after 30 days, plots 1 and 3 have completely deteriorated, whereas plots 2 and 4 are unaffected.

EXAMPLE 16

The following sprayings were carried out on 4 plots covered with herbaceous plants:
- Plot 1: glyphosate at 6 g/l (36 g of the solution to the m$^2$)
- Plot 2: glyphosate at 4.5 g/l (36 g of the solution to the m$^2$)
- Plot 3: a solution of glyphosate at 3 g/l+3-isononyloxypropane-1,2-diol at 0.9 g/l, in a proportion of 36 g of the solution to the m$^2$
- Plot 4: a solution of glyphosate at 1.5 g/l+3-isononyloxypropane-1,2-diol at 0.9 g/l, in a proportion of 36 g of the solution to the m$^2$.

It was observed that, after 30 days, plots 1 and 3 have completely deteriorated, whereas plots 2 and 4 are unaffected.

All these examples show that the glycerol ethers of formula (I) are accelerators of the deterioration in herbaceous plants, on the one hand, and that they decrease the amounts of herbicide(s) to be employed in carrying out a reading.

C—Demonstration of the Properties of Enhancing Fungicidal Effects of Glycerol Ethers In the following examples, the *Candida albicans* test strain used is sold under the reference ATCC 10231, Collection Institut Pasteur.

EXAMPLE 17

A *Candida albicans* strain was inoculated on agar in a Petri dish. Disks of blotting paper impregnated with the following solutions were subsequently deposited at its surface:
- disk 1 is impregnated with a solution comprising 0.8 of mancozeb
- disk 2 is impregnated with a solution comprising 0.5 g/l of mancozeb
- disk 3 is impregnated with a solution comprising 0.2 g/l of mancozeb
- disk 4 is impregnated with a solution comprising 0.2 g/l of mancozeb and 0.1 g/l of 3-butyloxypropane-1,2-diol.

The growth of *Candida albicans* was observed (in the middle of the dish) and also:
- around the disks 1 and 4: the formation was observed of circular regions of inhibition of the growth, close to each disk,
- around the disks 2 and 3: the absence was observed of an inhibition region.

EXAMPLE 18

A *Candida albicans* strain was inoculated on agar in a Petri dish. Disks of blotting paper impregnated with the following solutions were subsequently deposited at its surface:
- disk 1 is impregnated with a solution comprising 0.8 g/l of mancozeb
- disk 2 is impregnated with a solution comprising 0.5 g/l of mancozeb
- disk 3 is impregnated with a solution comprising 0.2 g/l of mancozeb
- disk 4 is impregnated with a solution comprising 0.2 g/l of mancozeb and 0.25 g/l of 3-pentyloxypropane-1,2-diol.

The growth of *Candida albicans* was observed (in the middle of the dish) and also:
- around the disks 1 and 4: the formation was observed of circular regions of inhibition of the growth, dose to each disk,
- around the disks 2 and 3: the absence was observed of an inhibition region.

EXAMPLE 19

A *Candida albicans* strain was inoculated on agar in a Petri dish. Disks of blotting paper impregnated with the following solutions were subsequently deposited at its surface:
- disk 1 is impregnated with a solution comprising 0.8 g/l of mancozeb
- disk 2 is impregnated with a solution comprising 0.5 g/l of mancozeb
- disk 3 is impregnated with a solution comprising 0.2 g/l of mancozeb
- disk 4 is impregnated with a solution comprising 0.2 g/l of mancozeb and 0.05 g/l of 3-(2-ethylhexyloxy)propane-1,2-diol.

The growth of *Candida albicans* was observed (in the middle of the dish) and also:
- around the disks 1 and 4: the formation was observed of circular regions of inhibition of the growth, close to each disk,
- around the disks 2 and 3: the absence was observed of an inhibition region.

These examples show that the glycerol ethers of formula (I) decrease the amounts of fungicide(s) to be employed in inhibiting the growth of fungi.

D—Demonstration of the Properties of Enhancing Insecticidal Effects of Glycerol Ethers In the following examples, flies of the species *Lucilia caesar* were obtained by having available pieces of minced meat and also about twenty maggots originating from a fly of the species *Lucilia caesar* (commercial origin, fishing item); after 5 days, cocoons are formed to give rise to the flies.

The aphids of the species *Sitobion avenae* used in the following examples were supplied by the Université de Picardie d'Amiens [University of Picardy of Amiens], laboratoire de biologie des plantes et contrôle des insectes ravageurs [Plant Biology and Insect Pest Control Laboratory], EA3900, 33, rue Saint Leu, Amiens 80000.

EXAMPLE 20

30 flies of the species *Lucilia caesar* were introduced into each of the cages made with a cubic frame from lengths of wood and mosquito screens. One of the faces was pierced with a hole through which a sprayer for the test solution is introduced:
- in cage 1, 1.8 g of a solution comprising 39.0 mg/l of diflubenzuron were sprayed
- in cage 2, 1.8 g of a solution comprising 39.0 mg/l of diflubenzuron and 47.0 mg/l of 3-isopropyloxypropane-1,2-diol were sprayed.

The degree of mortality of the population of flies in each cage was established:
- in cage 1, a degree of mortality of 29% was observed
- in cage 2, a degree of mortality of 64% was observed.

EXAMPLE 21

30 flies of the species *Lucilia caesar* were introduced into each of the cages made with a cubic frame from lengths of wood and mosquito screens. One of the faces was pierced with a hole through which a sprayer for the test solution is introduced:
- in cage 1, 1.8 g of a solution comprising 39.0 mg/l of diflubenzuron were sprayed in cage 2, 1.8 g of a solution comprising 39.0 mg/l of diflubenzuron and 47.0 mg/l of 3-(2-ethylhexyloxy)propane-1,2-diol were sprayed.

The degree of mortality of the population of flies in each cage was established:
in cage 1, a degree of mortality of 29% was observed
in cage 2, a degree of mortality of 56% was observed.

EXAMPLE 22

25 aphids of the species *Sitobion avenae* were introduced into a Petri dish into which the test solution was sprayed:
in dish 1, 1.8 g of a solution comprising 39.0 mg/l of diflubenzuron were sprayed;
in dish 2, 1.8 g of a solution comprising 39.0 mg/l of diflubezuron and 47.0 mg/l of 3-isopropyloxypropane-1,2-diol were sprayed.

The degree of mortality of the population of aphids in each cage was established:
in dish 1, a degree of mortality of 21% was observed
in dish 2, a degree of mortality of 4% was observed.

EXAMPLE 23

25 aphids of the species *Sitobion avenae* were introduced into a Petri dish into which the test solution was sprayed:
in dish 1, 1.8 g of a solution comprising 39.0 mg/l of diflubenzuron were sprayed;
in dish 2, 1.8 g of a solution comprising 39.0 mg/l of diflubenzuron and 47.0 mg/l of 3-pentyloxypropane-1,2-diol were sprayed.

The degree of mortality of the population of aphids in each cage was established:
in dish 1, a degree of mortality of 21% was observed
in dish 2, a degree of mortality of 81% was observed.

EXAMPLE 24

25 aphids of the species *Sitobion avenae* were introduced into a Petri dish into which the test solution was sprayed:
in dish 1, 1.8 g of a solution comprising 39.0 mg/l of diflubenzuron were sprayed;
in dish 2, 1.8 g of a solution comprising 39.0 mg/l of diflubenzuron and 47.0 mg/l of 3-hexyloxypropane-1,2-diol were sprayed.

The degree of mortality of the population of aphids in each cage was established:
in dish 1, a degree of mortality of 21% was observed
in dish 2, a degree of mortality of 67% was observed.

EXAMPLE 25

25 aphids of the species *Sitobion avenae* were introduced into a Petri dish into which the test solution was sprayed:
in dish 1, 1.8 g of a solution comprising 39, mg/l of diflubenzuron were sprayed;
in dish 2, 1.8 g of a solution comprising 39.0 mg/l of diflubenzuron and 47.0 mg/l of 3-(2-ethylhexyloxy)propane-1,2-diol were sprayed.

The degree of mortality of the population of aphids in each cage was established;
in dish 1, a degree of mortality of 21% was observed
in dish 2, a degree of mortality of 77% was observed.

EXAMPLE 26

25 aphids of the species *Sitobion avenae* were introduced into a Petri dish into which the test solution was sprayed:
in dish 1, 1.8 g of a solution comprising 39.0 mg/l of diflubenzuron were sprayed;
in dish 2, 1.8 g of a solution comprising 39.0 mg/l of diflubenzuron and 47.0 mg/l of 3-decyloxypropane-1,2-diol were sprayed.

The degree of mortality of the population of aphids in each cage was established:
in dish 1, a degree of mortality of 21% was observed
in dish 2, a degree of mortality of 60% was observed.

EXAMPLE 27

25 aphids of the species *Sitobion avenae* were introduced into a Petri dish into which the test solution was sprayed:
in dish 1, 1.8 g of a solution comprising 78.1 mg/l of pirimicarb were sprayed;
in dish 2, 1.8 g of a solution comprising 78.1 mg/l of pirimicarb and 62.5 mg/l of 3-methyloxypropane-1,2-diol were sprayed.

The degree of mortality of the population of aphids in each cage was established:
in dish 1, a degree of mortality of 16% was observed
in dish 2, a degree of mortality of 100% was observed.

EXAMPLE 28

25 aphids of the species *Sitobion avenae* were introduced into a Petri dish into which the test solution is sprayed:
in dish 1, 1.8 g of a solution comprising 78.1 mg/l of pirimicarb were sprayed;
in dish 2, 1.8 g of a solution comprising 78.1 mg/l of pirimicarb and 62.5 mg/l of 3-butyloxypropane-1,2-diol were sprayed.

The degree of mortality of the population of aphids in each cage was established:
in dish 1, a degree of mortality of 16% was observed
in dish 2, a degree of mortality of 100% was observed.

EXAMPLE 29

25 aphids of the species *Sitobion avenae* were introduced into a Petri dish into which the test solution was sprayed:
in dish 1, 1.8 g of a solution comprising 78.1 of pirimicarb were sprayed;
in dish 2, 1.8 g of a solution comprising 78.1 mg/l of pirimicarb and 62.5 mg/l of 3-pentyloxypropane-1,2-diol were sprayed.

The degree of mortality of the population of aphids in each cage was established:
in dish 1, a degree of mortality of 16% was observed
in dish 2, a degree of mortality of 87% was observed.

EXAMPLE 30

25 aphids of the species *Sitobion avenae* were introduced into a Petri dish into which the test solution was sprayed:
in dish 1, 1.8 g of a solution comprising 78.1 mg/l of pirimicarb were sprayed;
in dish 2, 1.8 g of a solution comprising 78.1 mg/l of pirimicarb and 62.5 mg/l of 3-hexyloxypropane-1,2-diol were sprayed.

The degree of mortality of the population of aphids in each cage was established:
in dish 1, a degree of mortality of 16% was observed
in dish 2, a degree of mortality of 92% was observed.

EXAMPLE 31

25 aphids of the species *Sitobion avenae* were introduced into a Petri dish into which the test solution was sprayed:
in dish 1, 1.8 g of a solution comprising 78.1 mg/l of pirimicarb were sprayed;

in dish 2, 1.8 g of a solution comprising 78.1 mg/l of pirimicarb and 62.5 mg/l of 3-decyloxypropane-1,2-diol were sprayed.

The degree of mortality of the population of aphids in each cage was established:

in dish 1, a degree of mortality of 16% was observed
in dish 2, a degree of mortality of 100% was observed.

These examples show that the glycerol ethers of formula (I) decrease the amounts of insecticide(s) to be employed to kill harmful insects in the crops concerned.

The invention claimed is:

1. A method for enhancing the biological effects of one or more herbicides, the one or more herbicides including at least one selected from glyphosate, glyphosate-isopropylammonium, and water-soluble glyphosate salts, the method comprising applying to a living plant a glycerol ether of formula:

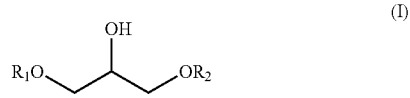

(I)

in which:
R$_1$ represents an alkyl group having from 1 to 18 carbon atoms;
R$_2$ represents a hydrogen atom or an alkyl group having from 1 to 18 carbon atoms, and
the one or more herbicides,
wherein the presence of the glycerol ether increases the rate of weed elimination and/or decreases the minimum amount of the one or more herbicides required to control weeds compared to the application of the one or more herbicides without the glycerol ether.

2. The method as claimed in claim 1, wherein the glycerol ether has the abovementioned formula (I) in which:
R$_1$ represents an alkyl group of formula $C_xH_{2x+1}$ where x=1 to 9;
R$_2$ represents an alkyl group of formula $C_yH_{2y+1}$ where y=0 to 8;
and $4 \le x+y \le 10$.

3. The method as claimed in claim 1, wherein the glycerol ether has the abovementioned formula (I) in which:
R$_1$ represents an alkyl group having from 4 to 9 carbon atoms; and
R$_2$ represents a hydrogen atom.

4. The method as claimed in claim 1, wherein the glycerol ether has the above-mentioned formula (I), in which:
R$_1$ represents a methyl or ethyl group; and
R$_2$ represents a methyl or ethyl group.

5. The method as claimed in claim 3, wherein the glycerol ether is selected from the group consisting of 3-pentyloxypropane-1,2-diol, 3-hexyloxypropane-1,2-diol and 3-(2-ethylhexyloxy)propane-1,2-diol.

6. The method as claimed in claim 1, wherein the one or more herbicides further comprises one or more selected from the group consisting of: dichlobenil; ethofumesate; glufosinate, glufosinate-ammonium; water-soluble glufosinate salts; isoproturon; linuron; metamitron; oxyfluorfen/propyzamide; phenmedipham and tifluralin.

7. The method of claim 1, wherein a plant-protection composition is applied and, comprises:
said one or more herbicides, and
said glycerol ether of formula (I).

8. The method as claimed in claim 7, wherein the composition comprises:
said one or more herbicides in an overall amount of 100 parts by weight; and
said glycerol ether of formula (I) in an overall amount of 5 to 200 parts by weight, expressed relative to the amount by weight of the one or more herbicides.

9. The method as claimed in claim 8, wherein the composition is provided in the form of a solution and comprises from 0.5 to 3 g/l of said glycerol ether of formula (I).

10. The method as claimed in claim 8, wherein the composition is provided in the form of a solution and comprises from 0.8 to 1 g/l of glycerol ether of formula (I).

11. The method of claim 7, comprising applying the plant-protection composition to a plant surface.

* * * * *